(12) United States Patent
Cobham

(10) Patent No.: US 7,625,577 B2
(45) Date of Patent: Dec. 1, 2009

(54) MATERIAL AND METHOD FOR TREATMENT OF TIMBER

(75) Inventor: Peter Raynor Soundy Cobham, Sunbury (AU)

(73) Assignee: KOPPERS-Hickson Timber Protection Pty Limited, North Sydney, New South Wales (AU)

( * ) Notice: Subject to any disclaimer, the term of this patent is extended or adjusted under 35 U.S.C. 154(b) by 900 days.

(21) Appl. No.: 10/865,041

(22) Filed: Jun. 10, 2004

(65) Prior Publication Data

US 2005/0008670 A1 Jan. 13, 2005

Related U.S. Application Data

(63) Continuation of application No. 10/460,931, filed on Jun. 13, 2003, now Pat. No. 7,361,215, which is a continuation-in-part of application No. PCT/AU01/01625, filed on Dec. 17, 2001.

(30) Foreign Application Priority Data

Dec. 15, 2000 (AU) .................................. PR2114

(51) Int. Cl.
*A01N 25/08* (2006.01)
(52) U.S. Cl. .................................. 424/409; 424/413
(58) Field of Classification Search ................ None
See application file for complete search history.

(56) References Cited

U.S. PATENT DOCUMENTS

| | | | |
|---|---|---|---|
| 2,561,380 A | 7/1951 | Kalberg et al. | 260/270 |
| 3,407,156 A | 10/1968 | La Berge | 260/22 |
| 3,837,875 A | 9/1974 | Murphy | 106/264 |
| 4,001,400 A | 1/1977 | Hager | 424/134 |
| 4,305,978 A * | 12/1981 | Hager | 427/351 |
| 4,360,385 A | 11/1982 | Grunewalder | 106/2 |
| 4,404,239 A | 9/1983 | Grunewalder | 427/393 |
| 4,750,934 A | 6/1988 | Metzner et al. | 106/18 |
| 4,783,221 A | 11/1988 | Grove | |
| 4,814,016 A | 3/1989 | Adkins et al. | 106/250 |
| 4,942,064 A | 7/1990 | Brayman et al. | 427/297 |

(Continued)

FOREIGN PATENT DOCUMENTS

CA 1305835 8/1992

(Continued)

OTHER PUBLICATIONS

Hickin, Norman E., The Woodworm Problem, 1972, Hutchinson & Co. Ltd, London.

(Continued)

*Primary Examiner*—Neil Levy
(74) *Attorney, Agent, or Firm*—Prout International IP, LLC

(57) ABSTRACT

A material and method for treating timber. The material comprises a preservative and a carrier. The carrier is selected such that it remains mobile within the wood and provides for migration of the preservative within the treated wood. By providing a carrier which is mobile within the wood, the timber has a 'self healing' effect wherein the carrier/preservative migrates to any freshly cut or exposed surface of the wood to thereby redistribute and treat such a surface within the preservative and hence maintain integrity of a treatment envelope surrounding the wood.

14 Claims, 6 Drawing Sheets

U.S. PATENT DOCUMENTS

| | | | |
|---|---|---|---|
| 4,950,329 A | 8/1990 | McIntyre et al. | 106/15.05 |
| 5,129,946 A | 7/1992 | Evans | 106/18.3 |
| 5,248,450 A | 9/1993 | Metzner et al. | |
| 5,397,795 A | 3/1995 | Valcke | 514/383 |
| 5,492,681 A | 2/1996 | Pasek et al. | 423/32 |
| 5,527,384 A | 6/1996 | Williams et al. | 106/18.32 |
| 5,607,633 A | 3/1997 | Sleeter et al. | 264/115 |
| 5,634,967 A | 6/1997 | Williams et al. | 106/18.32 |
| 5,719,301 A | 2/1998 | Sleeter | 554/24 |
| 5,804,591 A | 9/1998 | Valcke et al. | 514/383 |
| 5,824,370 A | 10/1998 | Bergervoet et al. | 427/297 |
| 5,916,356 A | 6/1999 | Williams et al. | 106/18.32 |
| 6,001,286 A | 12/1999 | Sleeter | 264/13 |
| RE36,798 E | 8/2000 | Williams et al. | 106/18.32 |
| 6,123,756 A | 9/2000 | Poppen et al. | 106/15.05 |
| 6,217,939 B1 | 4/2001 | Sailer et al. | 427/325 |
| 6,248,159 B1 | 6/2001 | Poppen et al. | 106/15.5 |
| 6,274,199 B1 | 8/2001 | Preston et al. | 427/298 |
| 6,464,764 B1 | 10/2002 | Lichtenberg et al. | 106/18.32 |
| 6,534,529 B2 | 3/2003 | Uhr et al. | 514/383 |
| 6,569,540 B1 | 5/2003 | Preston et al. | 428/537.1 |
| 6,576,175 B1 | 6/2003 | Roos | 264/109 |
| 6,641,927 B1 | 11/2003 | Honary | 428/536 |
| 6,642,392 B1 | 11/2003 | Basarab et al. | 548/561 |
| 6,653,324 B1 | 11/2003 | Kohler et al. | 514/315 |
| 6,686,056 B2 | 2/2004 | Roos et al. | 428/535 |
| 2003/0026942 A1 | 2/2003 | Hejna et al. | 428/107 |
| 2003/0108759 A1 | 6/2003 | Roos et al. | 428/537.1 |
| 2003/0176545 A1 | 9/2003 | Behling | 524/310 |
| 2003/0213401 A1 | 11/2003 | Cobham | 106/18 |
| 2005/0008670 A1 | 1/2005 | Cobham | |

FOREIGN PATENT DOCUMENTS

| | | |
|---|---|---|
| DE | 3004248 | 8/1984 |
| DE | 275 433 A1 | 1/1990 |
| DE | 275433 A1 | 1/1990 |
| DE | 40 36 508 | 7/1991 |
| DE | 4036508 A1 | 7/1991 |
| DE | 40 20 495 A1 | 10/1991 |
| DE | 4020495 A1 | 10/1991 |
| DE | 197 15 664 A1 | 10/1998 |
| DE | 198 41 271 A1 | 3/2000 |
| EP | 0 227 430 B1 | 7/1987 |
| EP | 0320531 A1 | 6/1989 |
| EP | 0 451 524 A1 | 3/1991 |
| EP | 0 576 608 B1 | 1/1992 |
| EP | 0472973 B1 | 5/1995 |
| EP | 0682091 A2 | 11/1995 |
| EP | 0897666 A1 | 2/1999 |
| EP | 0953634 A1 | 3/1999 |
| FR | 592 827 | 5/1925 |
| FR | 2 355 451 | 1/1978 |
| GB | 670258 | 4/1952 |
| GB | 1 564 188 | 4/1980 |
| GB | 1564188 A | 4/1980 |
| GB | 1 590 069 | 5/1981 |
| GB | 1 590 069 A | 5/1981 |
| JP | 63-68501 | 3/1988 |
| JP | 63068501 A2 | 3/1988 |
| JP | 8-012504 | 1/1996 |
| JP | 08118317 | 5/1996 |
| SE | 9602034 | 11/1997 |
| WO | WO-85/00040 A1 | 1/1985 |
| WO | WO 92/19429 | 11/1992 |
| WO | WO-92/19429 | 11/1992 |
| WO | WO-9219429 A1 | 11/1992 |
| WO | WO-96/10914 | 4/1996 |
| WO | WO-96/27483 A1 | 9/1996 |
| WO | WO 96/35560 | 11/1996 |
| WO | WO-02/47876 A1 | 6/2002 |
| WO | WO-03/047852 | 6/2003 |

OTHER PUBLICATIONS

Supplementary European Search Repost, Application No. EP 01 27 0411 2004.

Robinson, et al., "Wood preservation in the Australian beekeeping industry", (Apr. 24, 1988)—7 pages.

Grant et al., Grant & Hackh's Chemical Dictionary, Fifth Edition, McGraw-Hill, New York 1987, pp. 228 & 624.

"Australian Standard AS 3530-1988—Solvents—Minneral Turpentine and White Spirit", Published by Standards Association of Australia,(1988),10 pages.

"CD 50 Liquid Art—1997-1998", 5 pages.

"CD50 Liquid Art—Labels for Pails Used Before and After 2000", 3 pages.

"CD50 The Natural Finishing Touch—About 1992", 5 pages.

"Cutek From Chemisys Australia—Australian Label Post—2000", 4 pages.

"Pine Tar; History and Uses", http://www.maritime.org/conf/confkaye-tar.htm, (Observed Jul. 7, 1997), 5 pages.

Kropf, F. W., et al., "Comparative Weathering Tests of North American and European Exterior Wood Finishes", *Forest Products Journal*, 44(10), (Oct. 1994), 33-41.

Laks, P. E., et al., "Field Performance of Wood Preservative Systems in Secondary Timber Species", *The International Research Group on Wood Preservations, Section III Wood Protecting Chemicals*, (May, 1997), 1-12.

Permadi, P., et al., "Alternative Wood Preservatives for Use in Indonesia", *Forest Products Journal.*, 48(11/12), (Nov./Dec. 1998),98-101.

Richardson, B. A., *Wood Preservation*, 2nd Edition, E & FN Spon (1978), pp. 3, 143, 145 and 149.

Sandberg, D., "Solid-Color Stains on Western Redcedar and Redwood Siding", *The Finish Line—a Forest Products Laboratory Finishing Factsheet,*, Available on-line at http://www.fpl.fs.fed.us/finishing.htm,(1998),Two pages.

Smith, J. H., et al., *Principles of Wood Preservation (Information Series 10 of New Zealand Forest Service*, (1950), p. 33.

Unger, W., et al., "On the Resistance of Consolidated Ancient Wood Against Serpula Lacrymans (Wulfen: Fr) Schroeter", IRG/wp 00-10348, issued to the International Research Group on Wood Preservation,(2000), 1 page.

Williams, R. S., "Chapter 15 Finishing of Wood", *In the Wood Handbook*, (USDA, 1999) available online at http:/www.ftpl.fs.fed.us,(1999), 2 pages.

Williams, S., et al., "Selection and Application of Exterior Stains for Wood", *Forest Products Laboratory General Technical Report FPL-GTR-106*, United States Department of Agriculture, Forest Service,(Oct. 1995),Five Pages.

"Supplementary European Search Report, Application No. EP 01 27 0411", 4 pgs., Mar. 2005.

Osmose New Zealand, "Notice of Opposition to Grant of Patent (Section 21)", Filed by Osmose New Zealand in re: opposition to grant of New Zealand Patent Appln. No. 526240 (undated), 2 pgs., Aug. 2004.

Osmose New Zealand, "Statement of Case", By Osmose New Zealand in opposition to Application for Letters Patent No. 526240 (filed Aug. 25, 2004), 14 pgs.

Timtech Chemicals Limited, "Statement of Case", By Timtech Chemicals Limited in opposition to Application for Letters Patent No. 526240 (filed Aug. 25, 2004), 13 pgs.

Timtech Chemicalsl Limited, "Notice of Opposition to Grant of Patent (Section 21)", Filed by Timtech Chemicals Limited in re: Opposition to grant of New Zealand Patent Appln. No. 526240 (on or about Aug. 25, 2004), 2 pgs.

* cited by examiner

MATERIAL AND METHOD FOR TREATMENT OF TIMBER

RELATED APPLICATIONS

This application is a continuation application of U.S. patent application Ser. No. 10/460,931, filed Jun. 13, 2003, now U.S. Pat. No. 7,361,215, which is a continuation-in-part under 35 U.S.C. 111(a) of PCT/AU01/01625 filed Dec. 17, 2001 and published in English as WO 02/47876 on Jun. 20, 2002; which International Application claims priority from Australian Application No. PR 2114, filed Dec. 15, 2000; these applications and publications are incorporated herein by reference.

TECHNICAL FIELD

The present invention relates to preservatives and particularly preservatives for timber building materials.

BACKGROUND OF THE INVENTION

Wood continues to be the most commonly used framing material for the construction of residential properties. Its weakness to termite attack in some countries has been lessened by treatment of wood with insecticides. Application methods and approved chemicals vary dramatically through out the world.

Softwood timbers, *pinus radiata, pinus elliotti*, and *pinus carribea* used as framing timber in Australia are susceptible to termite attack. Changes to government regulations have limited the use of soil poisoning agents (banning of organo-chloride insecticides), which has led to a higher incidence of termite attack of timber framed houses.

Many countries including Australia and the USA are struggling to find suitable cost-effective methods to combat this ever-increasing risk of termite attack.

One of the strategies to combat termite attack of softwood frames is the treatment of the timber with insecticides or more broad-spectrum wood preservatives.

In Australia, for example, treatment of timber is covered by the Australian standard AS 1604-2000/. Hazard class H2 is defined for the biological hazard—borer and termites. Retention is measured in mass/mass (% m/m).

The approved chemicals are shown in the following table.

TABLE 1

| Minimum preservative retention in the penetration zone - Hazard Class 2 (H2) | | | | |
|---|---|---|---|---|
| Waterborne | | | | |
| Copper chrome arsenic (CU + Cr + As) | Ammoniacal copper quaternary (Cu + DDAC) | Light organic solvent preservatives | | |
| | | Permethrin | Cypermethrin | Deltamethrin |
| 0.320% m/m | 0.35% m/m | 0.020% m/m | 0.030% m/m | .0020% m/m |

Penetration is defined under the standard as—

"All preservative-treated wood shall show evidence of distribution of the preservative in the penetration zone in accordance with the following requirements:

(a) If the species of timber used is of natural durability class 1 or 2, the preservative shall penetrate all the sapwood. Preservative penetration of the heartwood is not required.
(b) If the species of timber used is of natural durability class 3 or 4, the preservative shall penetrate all of the sapwood and, in addition one of the following requirements shall apply.
 (i) Where the lesser cross-sectional dimension is greater than 35 mm, the penetration shall be not less than 8 mm from any surface. Where the lesser cross-sectional dimension is equal or less then 35 mm, the penetration shall be not less than 5 mm from any surface.
 (ii) Unpenetrated heartwood shall be permitted, provided that it comprises less than 20% of the cross-section of the piece and does not extend more than halfway through the piece from one surface to the opposite surface and does not exceed half the dimension of the side in the cross-section on which it occurs."

In order to provide for penetration of the preservative, a carrier must be used. As shown in the Australian standard, the carriers currently available are waterborne or solvent borne systems.

Waterborne carriers swell wood and hence timber thus treated needs to be re-dried prior to use in service. Australian Standards specify the maximum moisture content of pine framing. This level is around 12-14% moisture content.

The process sequence is:

Dry wood→treat→re-dry wood

Solvent borne preservatives because they are non-polar do not raise the moisture content and hence do not swell the wood.

The process sequence is:

Dry wood→solvent treat

The disadvantage of this treatment is the high cost of solvents and potential environmental concerns with volatile organic compounds (VOC's) being released into the atmosphere.

Application of the insecticides to wood is normally carried out by a batch process involving a pressure vessel. For waterborne preservatives a vacuum pressure process (Bethell or full cell) is used. This ensures, providing the wood is dry, complete sapwood penetration and adequate heartwood penetration if required.

For LOSP (light organic solvent preservatives) a double vacuum process ensures penetration to AS 1604-2000.

Pressure plants are expensive to construct, and being batch processes, conventional treatments do not match well with continuous sawmill production and require a high level of operator control to maintain costs.

The present invention seeks to overcome at least some of the disadvantages of the prior art or at least provide a commercial alternative thereto.

DISCLOSURE OF THE INVENTION

Figure 1:
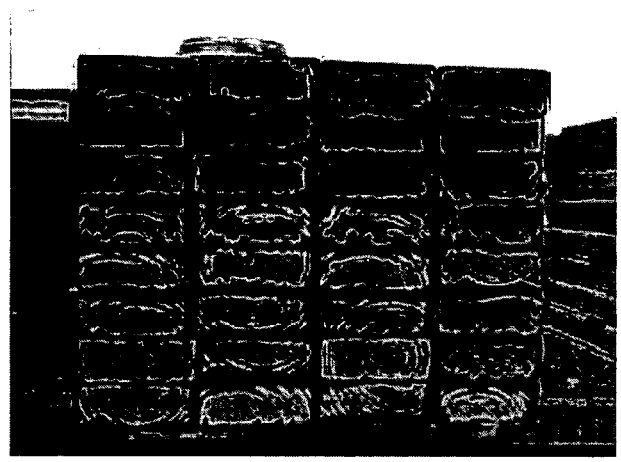
FIG. 1 shows the effect of the treatment on radiata heartwood, 24 hours after treatment.
Figure 2:
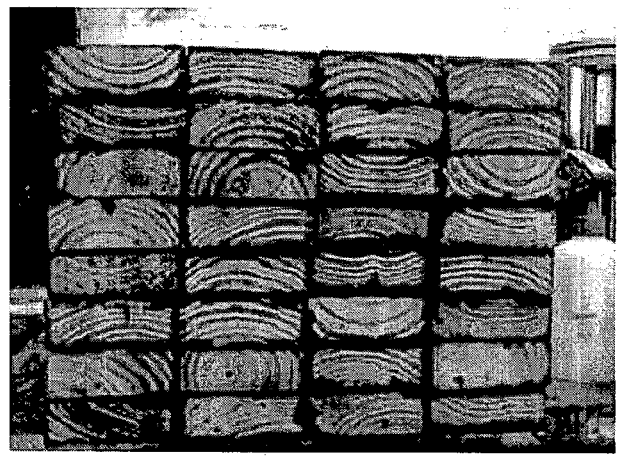
FIG. 2 shows the effect of the treatment on slash heartwood, 24 hours after treatment.
Figure 3:
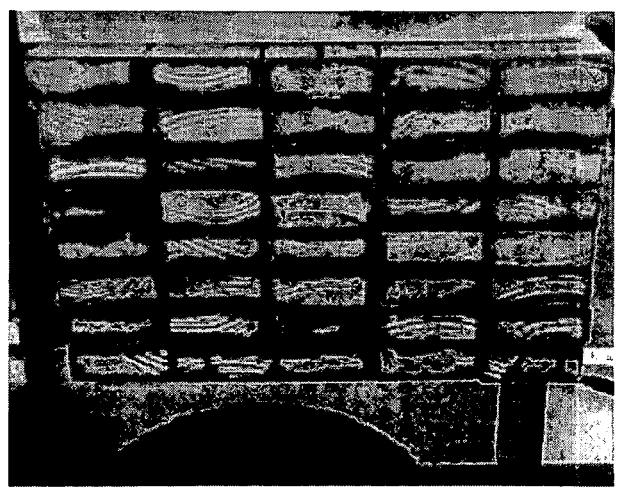
FIG. 3 shows the effect of the treatment on radiata sapwood 24 hours after treatment.
Figure 4:
FIG. 4 shows the effect of the treatment on slash sapwood, 24 hours after treatment.
Figure 5:
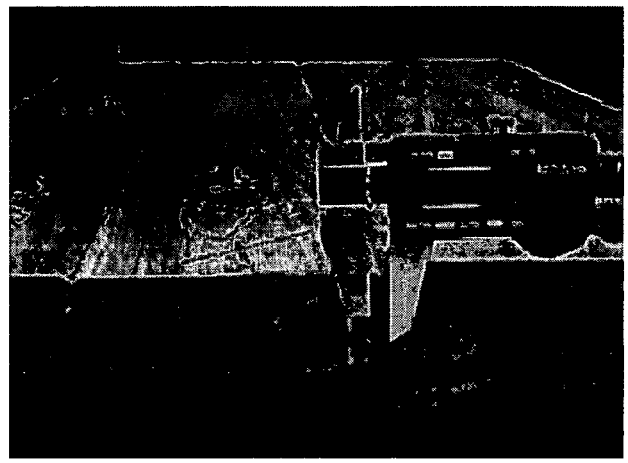
FIGS. 5 to 8 are close ups of the cut surface of the treated woods shown in FIGS. 1 to 4, respectively.
Figure 6:
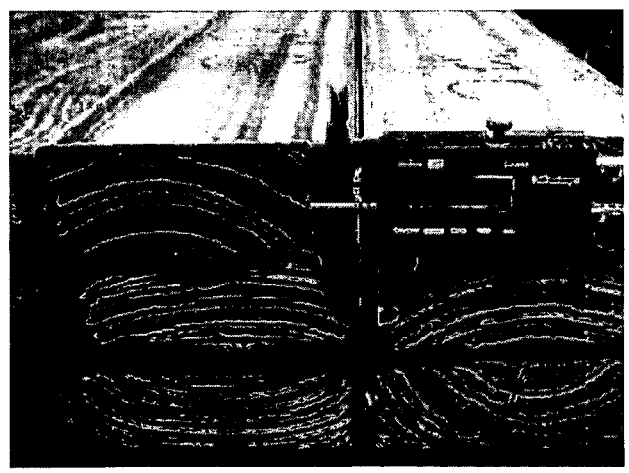
Figure 7:
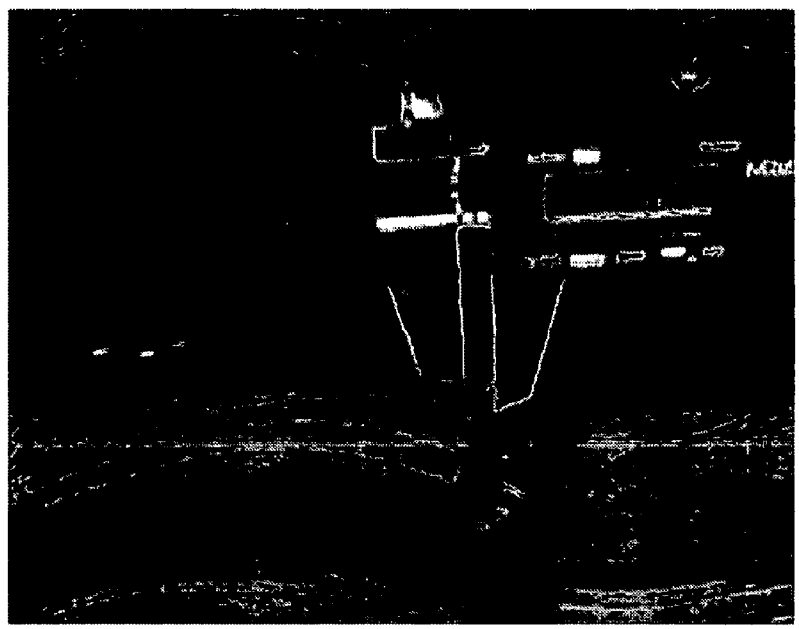
Figure 8:
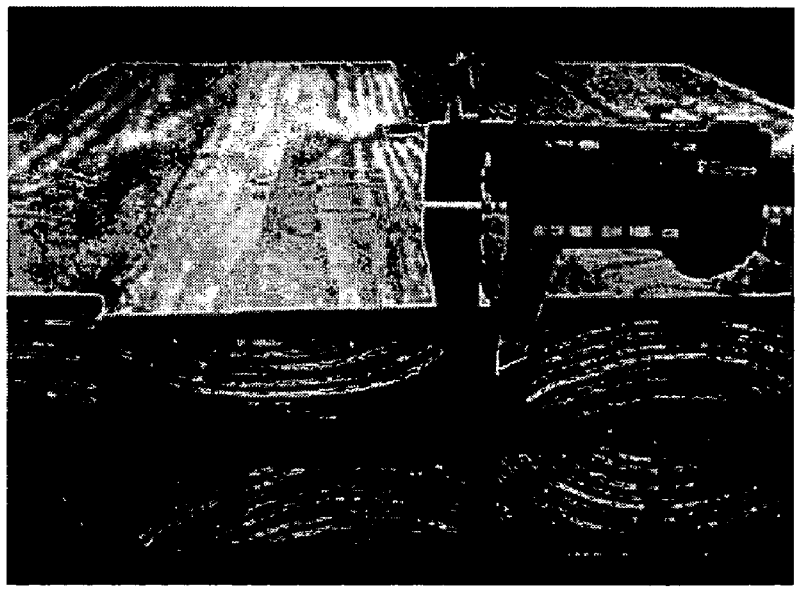
Figure 9:
FIGS. 9 to 12 show two stacks of the material. The lower stack are the treated wood shown in FIGS. 1 to 4 and the other stacks are the same material 24 hours later.
Figure 10:
Figure 11:
Figure 12:

In a broad aspect, the present invention comprises a material for treating wood comprising a preservative and a carrier, the carrier remaining mobile within the wood such that it provides for migration of the preservative within the treated wood.

In a further preferred embodiment, the carrier is a drying oil such as linseed oil or fish oil or any other drying oil, and may include extenders such as heating oil. These carriers remain mobile in the wood for a considerable period of time thereby allowing for migration of the preservative. The quantity of extender can between 90 to 10% of the total carrier, preferably 30 to 70% and most preferably 40 to 60%.

A wide variety of preservatives may also be used in combination with the carrier oil. Various insecticides and termidicides known in the art may be mixed with the oil including synthetic pyrethroid, permethrin, cypermethrin, imidacloprid etc.

Fungicides and mouldicides may also be used such as iodopropynylbutylcarbamate (IPBC), or 3-benzothien-2-yl-5,6-dihydro-1,4,2 oxathiazine-4-oxide (Bethoguard®); organic tin compounds such as tributyltin napthenate (TBTN); organic copper compounds such as copper 8 quinolinolate and copper napthenate, or bis-(N-cyclohexyldiazeniumdioxy) copper ("Cu-HDO"); organic zinc compounds; quaternary ammonium compounds, tertiary ammonium compounds, isothiazolones, triazoles such as tebuconazole, boron compounds. A preferred fungicide is 3-benzothien-2-yl-5,6-dihydro-1,4,2 oxathiazine-4-oxide (Bethoguard®) or bis-(N-cyclohexyldiazeniumdioxy) copper ("Cu-HDO"). This would allow the treatment material to be used as a permanent preservative as defined by Hazard classes 3, 4 and 5 in Australian Standard AS 1604-2000 America Wood Preservers Association (AWPA) standards (USA) and MP 3640 (New Zealand).

Drying agents such as cobalt, manganese, zirconium and copper naphthenate may be added to accelerate the drying of the drying oil.

The amount of the preservative/active constituent in the treatment material depends upon the preservative effect required but is expected to be below 5%, preferably below 2% and in many cases most preferably below 1%.

The applicant has found that the above mentioned material comprising a mixture of preservative and 'mobile' carrier provides an effective wood preservative which has a 'self healing' effect. Since the carrier remains mobile within the wood, it is capable of redistributing the active components of the preservative. This redistribution or migration of the carrier/preservative mixture will generally occur preferentially along the grain of the wood, however, some distribution across the grain will also occur. By providing such a migratable material, it is not necessary for the ends of the timber to be retreated after cutting since the active components of the material will be provided to the freshly cut ends with the migrating carrier oil.

Via this 'self healing' effect, the carrier/preservative migrates to any freshly cut or exposed surface of the wood to thereby redistribute and treat such a surface with the preservative and hence maintain integrity of the treatment envelope.

This is a significant advance over conventional preservative techniques. All previous techniques essentially treat the wood, are re-dried and then remain 'dormant' or fixed within the wood. The present inventive material and method provide a 'self healing' wood capable of retreating itself and in particular providing a preservative treatment to cut or damaged surface areas, which of course are the most common entry for termites.

Migration/penetration of the preservative system occurs in both radial and tangential directions forming an envelope around the treated wood. Such penetration in the tangential direction does not occur with water borne preservatives. Further, such migration ensures a consistency of the envelope around the surface of the treated wood. The envelope may be formed in both the heartwood and the sapwood and the aforementioned 'self healing' phenomenon also preferably occurs in the heartwood and the sapwood.

It will be recognised by persons skilled in the art that this self healing effect can be influenced by a number of parameters, for instance different carriers have different mobilities within the wood. Certain carriers may dry more quickly than others. Accordingly, the self healing effect will not be indefinite but tests have shown that this self healing effect will last from around a minimum of two to three weeks up to several months.

In a second embodiment, the present invention provides a method of treating wood comprising contact the wood with a mixture of preservative and carrier, the carrier remaining mobile within the wood such that it provides for migration of the preservative within the wood.

The treatment step can be conducted using conventional pressure application techniques such as existing vacuum pressure systems known in light organic solvent plants. Alternatively, the applicant has also found the mixture of the preservative and carrier can be applied without the need for pressure application. Treatment can be accomplished by spraying, dipping etc which, unlike previous conventional batch systems, is ideal for use on continuous production line facilities such as saw mills.

The applicant has also found that the proposed treatment material and method provides more than adequate protection without the need for complete sapwood penetration as required under the Australian Standard.

To explain, in one embodiment a protective envelope of preservative/carrier oil mixture with a depth of around 5 mm can be provided by simple dipping or spraying. This 5 mm envelope provides more than adequate protection from termite attack and, as mentioned above, allows migration of the preservative longitudinally through a timber board or beam to cover any end cuts. This of course is a major benefit over conventional techniques.

As discussed earlier, the Australian standard requires that, irrespective of the species of timber, ie natural durability class 1 to 4, the preservative shall penetrate all sapwood. The present invention does not require penetration of all sapwood. It uses an envelope type protection rather than penetration throughout the sapwood. This 5 mm envelope is a move away from conventional techniques but still provides adequate protection for treated timber and with the use of a preservative/mobile carrier oil results in the aforementioned self healing effect which of course is unknown with conventional techniques.

The most preferred carrier is linseed oil which is a drying oil, ie saturates in air. The linseed oil dries to form a water barrier and penetrates without the need for pressure. Advantageously, it is also low odour. Other drying oils such as fish oil may be used and other light weight hydrocarbons, eg heating oil may be used in limited quantities as an extender to the linseed or fish oil in order to reduce costs. Another advantage of the carrier oil is its high boiling point/flash point which reduces vapour emissions in production and use.

Another surprising benefit of using such a high boiling point carrier is its advantageous effect on migration of the preservative. To explain, it is believed that higher boiling point of the carrier/preservative mixture tends to allow the preservative to move inwards, as compared with more volatile solvents which migrate outwardly.

Indeed, the extender can also have a beneficial effect on the migration of the preservative. The extenders currently tested by the applicant have boiling points between about 175° C. and 300° C. These extenders remain quite mobile within the wood.

Preferably, the boiling point of the entire solvent/carrier system should remain above 62° C. While this is not essential it is preferred and suitable quantities of drying oils such as linseed or fish oil can be mixed with heating oil to obtain this boiling point.

Of course, using such a non-swelling drying carrier oil also has the advantage that the treated wood/timber does not need to be re-dried, ie treatment can be accomplished by simple dipping of the wood for periods of say up to one minute. Current trials with radiata and slash pine have both achieved 5 mm envelope penetration within about five to 60 seconds dipping time.

It is envisaged that other carrier oils may also be used provided, that when mixed with the preservative they remain mobile within the wood to allow migration of the preservative.

BEST MODE FOR CARRYING OUT THE INVENTION

Tests were conducted to verify the efficacy of the above mentioned process, including the mobility and self healing characteristics of the preservative/carrier system previously described.

Example 1

Radiata heartwood, radiata sapwood, slash heartwood and slash sapwood was sourced from various suppliers. Boards measuring 35 mm×90 mm×4.8 meters were cut into four separate 1 meter lengths. Boards measuring 35 mm×90 mm×2.4 meters were cut into two separate 1 meter lengths. A drying oil (linseed oil) used in combination with an extender (heating oil) was used (ratio of linseed oil to extender 50:50). The preservative formulation also had an addition of 0.01% (m/m) copper (present as copper naphthenate) as an indicator of the penetration. The test was conducted by firstly weighing the boards, and then dipping the board, in a mixture of the preservative formulation with 0.01% (m/m) copper (present as copper naphthenate) for 1 minute. They were allowed to drip until dry to the touch. Boards were then weighed again and stacked for 24 hours before being cut in half. The exposed surface on one half of the board was sprayed with indicator solution and photographed.

As shown in Table 2 resultant weights taken both before and after treatment show average uptakes for radiata heartwood at 18 $l/m^3$, 20 l/m3 for radiata sapwood, 16 $l/m^3$ for slash heartwood and 18 $l/m^3$ for slash sapwood. Standard deviations were low and the coefficient of variation was less than 20 in all but the slash heartwood. This indicates that there is little variability in uptake of preservative into radiata heartwood and sapwood, and slash sapwood.

TABLE 2

Example 1: Uptake Results (60 Second Dip)

| Wood Type | Uptake | StDev | Coeff of Var |
|---|---|---|---|
| Radiata heartwood | 17.89 | 3.5 | 19.67 |
| Radiata sapwood | 19.97 | 3.5 | 17.65 |
| Slash heartwood | 16.36 | 5.35 | 32.73 |
| Slash sapwood | 18.35 | 2.9 | 15.9 |

The attached figures show the effect of the treatment on radiata heartwood, radiata sapwood, slash heartwood and slash sapwood at various times after treatment as follows:

FIGS. 1 to 4 show radiata heartwood, slash heartwood, radiata sapwood and slash sapwood respectively 24 hours after treatment, FIGS. 5 to 8 are close ups of the cut surface of the material shown in FIGS. 1 to 4 respectively, and FIGS. 9 to 12 show two stacks of the material, the lower stack being that shown in FIGS. 1 to 4 and the other stacks being the same material 24 hours later.

As shown in FIGS. 1 to 4 and more clearly in FIGS. 5 to 8, the inventive process provided a consistent 5 mm envelope of penetration through the radiata heartwood, radiata sapwood and slash sapwood. A few of the slash heartwood samples did not show such a 5 mm envelope.

All samples, however, showed the migration of the treatment material ('self healing' effect) 24 hours later. FIGS. 9 to 12 provide an excellent comparison of mobility/penetration within 24 hours. Each figure has two stacks as mentioned above. The bottom stack is the material shown in FIGS. 1 to 4. The top stack is the radiata/slash heartwood/sapwood 24 hours after end cuts. The increased penetration of the carrier/preservative is clearly evident. The migration of the treatment material and self healing effect is most obvious in the radiata sapwood shown in FIG. 11 and radiata heartwood shown in FIG. 9.

Example 2

In Example 1, the treatment process involved a 60 second dip. Trials with *pinus elliotti* (slash pine) have shown that treatment times can be reduced to as low as five seconds without effecting penetration or retention. Treatment uptake depends on the profile used with rougher headed material giving uptakes 10 to 15% higher than smooth dress material.

In addition, these trials have shown that packs can be treated in their final shape and form, ie tightly block strapped, without effecting uptake and penetration.

The table below shows the correlation between dipping time and average uptake. As is clear from this example, dip times as low as five seconds can provide sufficient uptake of carrier/preservative mixture for efficient generation of the protective envelope. This is even true, as mentioned above, with packs of tightly strapped material. In this case packs of 95×45 mm timber were used stacked six high and five wide.

TABLE 3

Example 2: Uptake Results (Dip time Variation)

| Species | Profile | Dip Time (sec) | Average uptake (l/m3) | % coeff of variation |
|---|---|---|---|---|
| Slash Pine | Rougher headed | 60 | 25 | 28 |

TABLE 3-continued

Example 2: Uptake Results (Dip time Variation)

| Species | Profile | Dip Time (sec) | Average uptake (l/m3) | % coeff of variation |
|---|---|---|---|---|
| Slash Pine | Rougher headed | 45 | 30 | 34 |
| Slash Pine | Rougher headed | 30 | 26 | 32 |
| Slash Pine | Rougher headed | 5 | 18 | 22 |
| Slash Pine | Rougher headed | 5 | 17 | 21 |

Example 3

This example related to the treatment of Douglas fir. Douglas fir (*psuedotsuga menziesii*) is an inherently difficult species to treat. Trials with this species using the above mentioned formulation have shown penetration in both the hardwood and sapwood similar to pine species. The treatment process involved a 60 second immersion in a preservative carrier mix, where the carrier was at 50:50 mix of linseed oil and heating oil.

Average uptakes for 100×50 and 150×50 were around 20 L/m³. A well defined envelope was formed in both the heartwood and sapwood.

Accordingly, it can be seen from this example that the inventive treatment may be applied to a wide variety of timber products.

Example 4

In addition to sawn timber, the treatment material and process is suitable for composite products. Treatment trials have been carried out with various wood composite to assist uptake and penetration, ie formation of the preservative envelope. Composites treated include particle board, plywood, medium density fibre board (MDF) and oriented strand board (OSB).

The treatment process was similar to the above, ie a 60 second immersion.

Details over these tests are given under Table 4.

TABLE 4

Example 4: Uptake Results (Composite Products)

| Wood Type | Uptake | Std dev | % CV |
|---|---|---|---|
| Particle Board | 29.4 | 6.2 | 21.1 |
| Plywood | 37.2 | 7.7 | 20.6 |
| MDF | 14.3 | 0.6 | 4.1 |
| OSB | 85.9 | 8.9 | 10.3 |

Example 5

The examples above were conducted using oil mixtures as the carrier. Tests have also being conducted using water-in-oil emulsions including up to 30% water. If desired, emulsifiers in the form of non-ionic surfactants can also be added to the emulsifier.

It has been found that such formulations gave similar envelopes of penetration with similar uptakes. Advantageously, wood swelling was minimal at these concentrations of water.

TABLE 5

Example 5: Uptake Results (Water in Oil Emulsion)

| Species | Profile | Dip Time (sec) | Average uptake (l/m3) | % coeff of variation |
|---|---|---|---|---|
| Radiata pine | Rougher headed | 60 | 21 | 26 |
| Radiata pine | Rougher headed | 30 | 19 | 22 |
| Radiata pine | Rougher headed | 15 | 19 | 30 |
| Radiata pine | Rougher headed | 5 | 15 | 28 |

As can be seen from Table 5 above, using water in oil emulsions also give sufficient uptake of the carrier/preservative mixture to provide suitable treatment. It is also noted that with water in oil emulsions, the uptake between five second dip times and 60 second tip times is even less than previous examples.

Example 6

Further tests were conducted on the susceptibility of the treated blocks to termite attack.

Commercial-size-section (35×90 mm) material of both slash and radiata pine were treated with the described material and supplied as 1 m lengths. One hundred and forty test blocks (35×90×190 mm long) were used; one block cut from each 1 m length supplied. Twenty-eight treatments (including 16 with block ends treated) with 5 replicates were exposed in plastic food containers to termites foraging in trenches at Beerburrum, south-east Queensland, Australia. Radiata pine control blocks were also exposed in plastic food containers to monitor termite foraging vigour on each trench. Following exposure for 29 weeks, mass losses of the blocks were estimated, analysed and reported.

On 3 of the 4 trenches, *C. acinaciformis* or *Schedorhinotermes seclusus*, or both provided a severe termite foraging pressure. Termites did not forage on the remaining trench, which had been used recently for other work and the absence of termites may have been a "carry-over" effect. We have not observed this phenomenon before. On the other trenches, the termites entered the vast majority of boxes, but essentially damaged only untreated and solvent test blocks and feeder blocks (see Table). All treatments appeared to protect the test blocks. Exposing cut untreated ends to the termites did not promote termite foraging on these blocks and there appeared no need to treat the ends of the test blocks with treatment material, with regard to *C. acinaciformis*. Industry, however, should be cognisant of differences in foraging behaviour between termite genera, and perhaps between termite species, as the commercialisation of the envelope treatment processes develops.

The below table outlines the results of these tests. The severity of the test protocol is evidenced by the amount of termite damage to the control blocks, (ie those treated with solvent only) in the control boxes and by the amount of fungal decay in some of the test boxes. The termite foraging pressure was severe and conditions suitable for sustained termite foraging and supportive of fungal decay.

Those blocks treated by the present invention, ie Permethrin or Delta envelopes resisted both termite attack and fungal decay very well compared with conventional techniques, eg Permethrin, LOSP (light organic solvent preservative).

The Delta/Permethrin compounds are conventional insecticides/termidicides used in Australia.

TABLE 6

Summary of Termite Trial

| Box No. | Species | Heart/sap | Treatment | Test | Feeder | Trench |
|---|---|---|---|---|---|---|
| 1 | Radiata | Heartwood | Untreated | Fail*** | Fail*** | 1 |
| 2 | Radiata | Heartwood | Permethrin envelope | Pass | Fail** | 2 |
| 5 | Radiata | Heartwood | LOSP Permethrin | Pass | Fail*** | 2 |
| 22 | Radiata | Heartwood | Permethrin envelope | Pass | Fail* | 1 |
| 21 | Radiata | Heartwood | Delta envelope | Pass | Fail* | 1 |
| 8 | Radiata | Sapwood | Solvent | Fail* | Fail* | 4 |
| 9 | Radiata | Sapwood | Delta envelope | Pass | Pass | 2 |
| 10 | Radiata | Sapwood | LOSP Permethrin | Pass | Fail** | 4 |
| 11 | Slash | Heartwood# | Untreated | Fail*** | Fail*** | 2 |
| 12 | Slash | Heartwood | Permethrin envelope | Pass | Fail** | 4 |
| 25 | Slash | Heartwood | Permethrin envelope | Pass | Fail** | 2 |
| 15 | Slash | Heartwood | Permethrin LOSP | Pass | Fail*** | 1 |
| 13 | Slash | Heartwood | Solvent | Pass | Fail* | 4 |
| 14 | Slash | Heartwood | Delta envelope | Pass | Fail*** | 4 |
| 26 | Slash | Heartwood | Delta envelope | Pass | Pass | 1 |
| 16 | Slash | Sapwood | Untreated | Fail*** | Fail*** | 2 |
| 17 | Slash | Sapwood | Permethrin envelope | Pass | Fail*** | 1 |
| 19 | Slash | Sapwood | Delta envelope | Pass | Fail* | 1 |
| 20 | Slash | Sapwood | Permethrin LOSP | Pass | Fail** | 2 |
| 23 | Slash | Sapwood | Permethrin envelope | Pass | Fail** | 4 |
| 24 | Slash | Sapwood | Delta envelope | Pass | Fail* | 4 |
| 3 | Radiata | Heartwood | Solvent | N/A | N/A | 3^ |
| 4 | Radiata | Heartwood | Delta envelope | N/A | N/A | 3^ |
| 6 | Radiata | Sapwood | Untreated | N/A | N/A | 3^ |
| 7 | Radiata | Sapwood | Permethrin envelope | N/A | N/A | 3^ |
| 27 | Radiata | Sapwood | Permethrin envelope | N/A | N/A | 3^ |
| 28 | Radiata | Sapwood | Delta envelope | N/A | N/A | 3^ |
| 18 | Slash | Sapwood | Solvent | N/A | N/A | 3^ |

Figure 13:
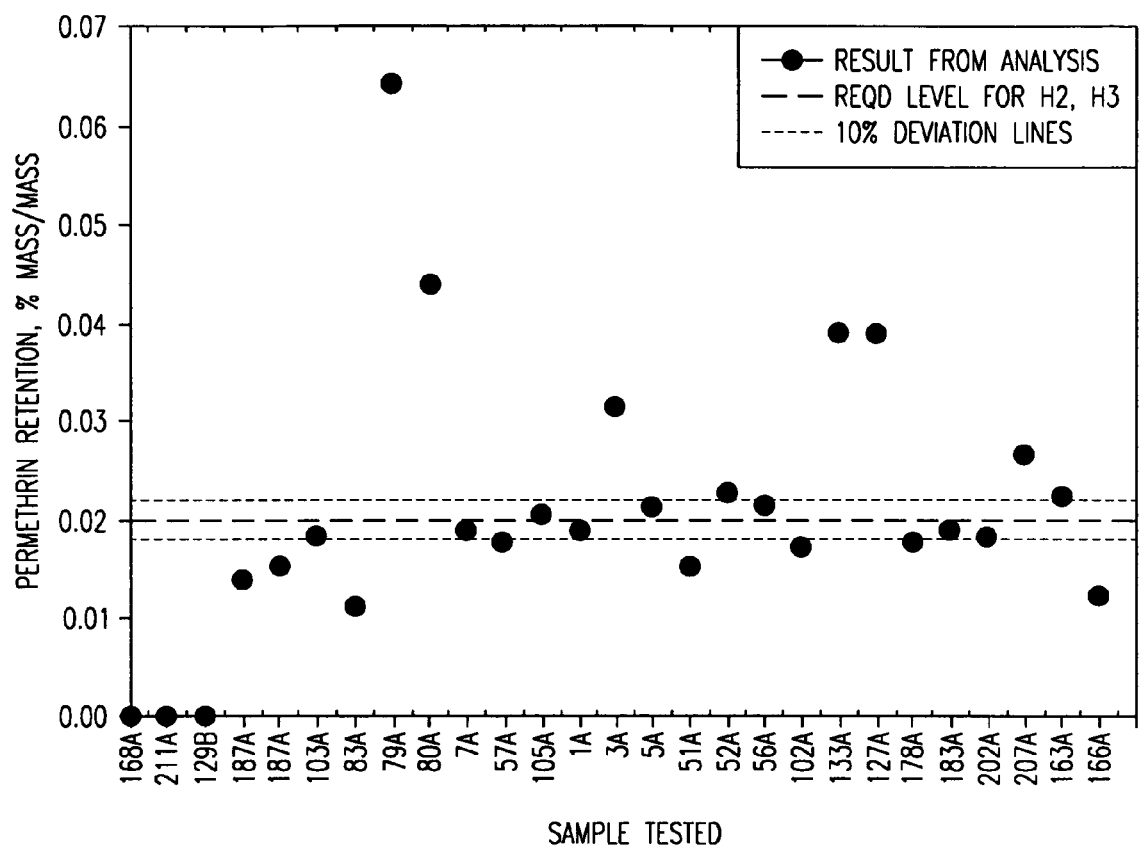
FIG. 13 shows the results of tests conducted on samples prepared in example 6.

Test blocks with ends treated
*Attacked
**Moderate attack
***Severe attack
High sapwood content
^Lack of termite activity (trench had been used previously for boron trial)
N/A Not Applicable Additional tests were conducted on the various samples from Example 6 and they are provided under FIG. 13. This test was to determine the permethrin retention in the outer 5 mm of the treated samples. As mentioned above, the disclosed treatment provides an envelope around the timber which acts as a barrier to termite and fungal attack.

The Australian Standard AS 1604 for insecticide/termidicide content is 0.02%. Samples 168A, 211A and 129B were control blends and hence were not treated with permethrin. As can be seen from the remaining samples, however, most fell within or above the 0.02% standard (10% deviation).

The Applicant's target was to treat only the outer 5 mm of the wood within the 0.02% permethrin retention. This is in contrast to the Australian Standard AS1604 which calls for complete sapwood penetration and in the case of radiata pine, 5 mm heartwood penetration. The 5 mm envelope was achieved in both heartwood and sapwood of the radiata. For slash pine, where only sapwood penetration is required, a 5 mm envelope was also achieved.

Accordingly, it can be seen that the inventive material and treatment method provide not only adequate protection but does so in a more efficient and cost effective manner than conventional techniques.

INDUSTRIAL APPLICABILITY

It can be seen that the present invention provides a significant advantage over the prior art. The aforementioned discussion should in now way limit the scope of the invention and various other embodiments can be provided without departing from the spirit or scope of the invention.

All publications, patents, and patent documents, cited in this application, are herein incorporated by reference, as though individually incorporated by reference.

The invention claimed is:

1. A treated wood product consisting of:
   a) wood or a wood composite consisting of particles, fibres, plies, strands or mixtures thereof;
   b) an organic copper compound and an insecticide, and
   c) a carrier consisting of a drying oil and an extender oil, wherein the copper compound is copper 8 quinolinolate, copper naphthenate, or bis-(N-cyclohexyldiazenium-dioxy) copper and the insecticide is a pyretbroid, or imidacloprid;
   wherein the copper compound is present in said wood in an amount effective to be a permanent preservative of the treated wood.

2. The treated wood product of claim 1, wherein the product is particle board, solid board, plywood, medium density fibre board, or oriented strand board.

3. The treated wood product of claim 2, wherein the drying oil is non swelling.

4. The wood product of claim 1, wherein the pyrethroid is permethrin, deltamethrin, or cypermethrin.

5. The treated wood product of claim 2, wherein the treated wood product is solid boards, particle boards or plywood.

6. The treated wood product of claim 2, wherein the drying oil is linseed oil and the extender oil is heating oil.

7. Treated wood consisting of
   a) wood plies;
   b) an organic copper compound and an insecticide, and c) a carrier consisting of a drying oil and an extender oil,
wherein the copper compound is copper 8 quinolinolate, copper naphthenate, or bis-(N-cyclohexyldiazeniumdioxy) copper and the insecticide is a pyrethroid, or imidacloprid;
wherein the copper compound is present in said wood in an amount effective to be a permanent preservative of the treated wood.

8. The wood product of claim 7, wherein the pyrethroid is permethrin, deltamethrin, or cypermethrin.

9. The treated wood of claim 8, wherein the wood is plywood.

10. The treated wood product of claim 1, wherein the wood composite consists of wood particles.

11. The treated wood of claim 10, wherein the copper compound content in the mixture is below 5%.

12. The treated wood of claim 11, wherein the copper compound content in the mixture is below 2%.

13. The treated wood of claim 12, wherein the copper compound content in the mixture is below 1%.

14. The treated wood product of claim 5, wherein the product is a plywood.

* * * * *